United States Patent
Tu et al.

(10) Patent No.: US 7,829,272 B2
(45) Date of Patent: Nov. 9, 2010

(54) VIRAL DETECTION LIPOSOMES AND METHOD

(75) Inventors: Eugene Tu, San Diego, CA (US); Donald E. Ackley, Cardiff, CA (US); Anita Forster, Santee, CA (US); Michael Krihak, Rohnert Park, CA (US)

(73) Assignee: Nanotrope Inc., Cardiff, CA (US)

( * ) Notice: Subject to any disclaimer, the term of this patent is extended or adjusted under 35 U.S.C. 154(b) by 453 days.

(21) Appl. No.: 11/753,533

(22) Filed: May 24, 2007

(65) Prior Publication Data

US 2009/0148828 A1 Jun. 11, 2009

(51) Int. Cl.
*C12Q 1/68* (2006.01)
*C12Q 1/70* (2006.01)
*C12Q 1/02* (2006.01)

(52) U.S. Cl. ............... 435/5; 435/6; 435/29; 428/402.2; 536/24.32

(58) Field of Classification Search ............. None
See application file for complete search history.

(56) References Cited

U.S. PATENT DOCUMENTS

| | | | |
|---|---|---|---|
| 4,661,442 | A | 4/1987 | Lukens |
| 2004/0248188 | A1 | 12/2004 | Sanders |
| 2005/0123935 | A1 | 6/2005 | Haugland et al. |
| 2006/0275854 | A1 | 12/2006 | Li et al. |
| 2007/0269459 | A1 | 11/2007 | Coll Morales et al. |
| 2008/0248492 | A1 | 10/2008 | Yamazaki et al. |
| 2008/0303415 | A1 | 12/2008 | Suzuri et al. |

OTHER PUBLICATIONS

Tyagi and Kramer. Molecular Beacons: Probes that Fluoresce upon Hybridization, Nature Biotechnology. 1996; 14:303-308.*
Spear, PG. Herpes simplex virus: receptors and ligands for cell entry. Cellular Microbiology. 2004; 6(5):401-410.*
Medina-Kauwe, LK. Endocytosis of adenovirus and adenovirus capsid proteins. Advanced Drug Delivery Reviews. 2003; 55: 1485-1496.*
Lakadamyali, et al. Endocytosis of influenza viruses. Microbes and Infection. 2004; 6:929-936.*
Kido, et al. Proteases Essential for Human Influenza Virus Entry into Cells and Their Inhibitors as Potential Therapeutic Agents. Current Pharmaceutical Design. 2007;13:405-414.*
Lopez and Arias. Multistep entry of rotavirus into cells: a Versaillesque dance. TRENDS in Microbiology. 2004; 12(6): 271-278.*
Wittlich, et al. Expression, purification, and membrane reconstitution of a CD4 fragment comprising the transmembrane and cytoplasmic domains of the receptor. Protein Expression and Purification. 2007; 55:198-207.*

* cited by examiner

*Primary Examiner*—Mary E Mosher
*Assistant Examiner*—Stuart W Snyder
(74) *Attorney, Agent, or Firm*—Parsons & Goltry; Robert A. Parsons; Michael W. Goltry

(57) ABSTRACT

A method of generating pathogen detecting liposomes includes a step of providing molecular beacons with fluorescing components. The molecular beacons include either strands of RNA or DNA and the fluorescing components include an emitter and a quencher. The method further uses nanodroplet technology to encapsulate the molecular beacons within a lipid membrane. Subsequently, receptors are assembled in association with the membrane.

10 Claims, 2 Drawing Sheets

VIRAL DETECTION LIPOSOMES AND METHOD

FIELD OF THE INVENTION

Figure 1:
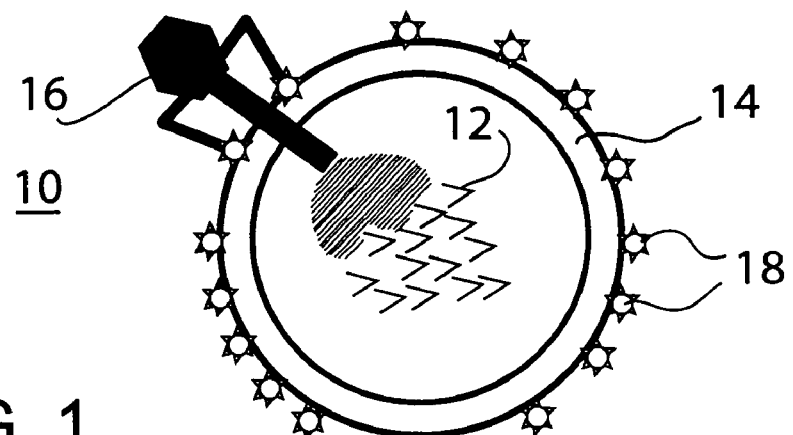

This invention relates to specifically engineered liposomes and methods of use for the detection of viral pathogens and the like including unknown, mutated, or engineered varieties.

BACKGROUND OF THE INVENTION

The detection and assaying of viral pathogens is very complicated and labor intensive. At a time when new and different viral pathogens appear regularly and with increasing frequency, the detection and identification, as well as improved methods and apparatus for collection, as quickly and efficiently as possible are highly desirable. This of course is true for mutated and engineered varieties as well as any unknown varieties. At the present time, the only known method for detection and identification is by processing collected viral pathogens in a laboratory using well known testing or trial-and-error procedures such as cell cultures or PCR.

It would be highly advantageous, therefore, to remedy the foregoing and other deficiencies inherent in the prior art.

Accordingly, it is an object of the present invention to provide new and improved viral detection liposomes and methods of use.

Also, it is an object of the present invention to provide new and improved viral collection liposomes and methods of collection.

SUMMARY OF THE INVENTION

Briefly, to achieve the desired objects of the present invention in accordance with a preferred embodiment thereof, provided is a method of generating pathogen detecting liposomes including the steps of providing a means of detecting genetic material, encapsulating the means of detecting genetic material within a lipid membrane, and assembling receptors in association with the membrane. Also, the means of detecting genetic material can be left out and the receptor carrying liposome simply used to collect genetic material for later use.

Also, to achieve the desired objects of the present invention, provided is a more specific method of generating pathogen detecting liposomes that includes a step of providing molecular beacons with fluorescing components. The molecular beacons include either strands of RNA or DNA and the fluorescing components include an emitter and a quencher. The method further uses nanodroplet technology to encapsulate the molecular beacons within a lipid membrane. Subsequently, receptors are assembled in association with the membrane.

The objects and other aspects of the invention are further achieved by a method of generating pathogen detecting liposomes using nanodroplet technology. A droplet generator is provided with a carrier fluid inlet, a focusing fluid inlet, and an outlet for focusing fluid and droplets. A carrier fluid is formed including water and molecular beacons and a focusing fluid is formed including a solvent, lipids and surface ligands or receptors as desired. Alternatively, the focusing fluid may contain other materials such as polymers, carbohydrates, or proteins to form alternative membrane structures. In addition, transmembrane proteins, ion channels, or the like may be included to form receptors. The carrier fluid is injected into the carrier fluid inlet and the focusing fluid is injected into the focusing fluid inlet so as to form vesicles having molecular beacons encapsulated within a lipid membrane. A bilayer membrane is further achieved through a templating process whereby the focusing fluid is exchanged for an aqueous medium in the presence of excess lipids. Receptors are assembled in association with the membrane, either embedded in or attached to the membrane.

The objects and other aspects of the invention are further achieved by a pathogen detecting liposome with a lipid membrane encapsulating a plurality of molecular beacons including fluorescing components. Receptors are assembled in association with the membrane, either embedded in or attached to the membrane.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings; in which:

FIG. 1 is a schematic depiction of an embodiment of a viral detection liposome in accordance with the present invention;

FIG. 2 is a simplified schematic diagram of a liposome generator used in the formation and engineering of the viral detection liposomes;

FIG. 3 is a simplified diagram of a following procedure in the phase inversion technique; and FIGS. 4*a*-*d* illustrate examples of molecular beacons.

DESCRIPTION OF THE PREFERRED EMBODIMENT

The disclosed novel detection methods for a viral identification assay are based on mimicking the response mechanisms similar to those found in living cells. By tailoring or engineering liposomes with the appropriate biomolecular and biochemical compositions these particles are comprised of the necessary biological elements to sense and identify potential biological threats. The application of nanodroplet technology provides customized liposomes that are packaged with the suitable binding substrates, biochemical reagents, and optical reporters. These liposomes are functionalized with pre-determined surface receptors that specifically target conserved characteristics of unknown or engineered pathogens of certain biological classes. Due to the flexible nature of the nanodroplet technology for providing various liposome compositions on demand, this approach has significant impact in the rapid development and deployment of reagents and receptor molecules for integration into existing detection systems. In addition to improvements in assay speed, accuracy, and sensitivity, the engineered liposomes also operate in complex backgrounds and provide the detection capability of multiple pathogens simultaneously. By appropriate choice of the binding substrates, biological threats including viruses and bacteria, and molecular markers such as proteins, peptides, antigens, toxins, and various small molecules can be analyzed. Of particular interest is the analysis of viral RNA for the detection of viral pathogens, using genetic substrates contained within the liposomes, and lipid membranes optimized for viral capture.

The structure of the engineered liposomes is relatively simple and is depicted schematically in FIG. 1. Using the nanodroplet technology (described in more detail below), strands of RNA or DNA configured as molecular beacons 12 are encapsulated in the interior of a lipid shell 14 of liposome 10. Molecular beacons 12 will target the conserved sequences found across the wide range of influenza strains, for example. Fluorescence from molecular beacons 12 is activated when matching genetic material from a viral target 16 hybridizes to a molecular beacon or beacons 12. In a preferred embodiment fluorescence intensity is enhanced using metallic particles or quantum dots to substantially increase the assay sensitivity. Surface receptors 18 are attached to lipid shell 14 to form binding sites for viral target 16. When viral target 16 binds to surface receptors 18, within a short amount of time it will "inject" its genetic material, generally RNA but sometimes DNA, into the interior of liposome 10 by fusion with the lipid membrane, where the genetic material is able to hybridize to one or more molecular beacons 12, activating the fluorescence signal. The entire process of viral fusion and hybridization generally occurs within approximately 360 seconds. By encapsulating molecular beacons 12 within liposomes 10, whose size is similar to cells and monodisperse, the use of commercial Fluorescence Activated Cell Sorter (FACS) instrumentation for high speed analysis and sorting of liposomes is enabled.

Figure 2:
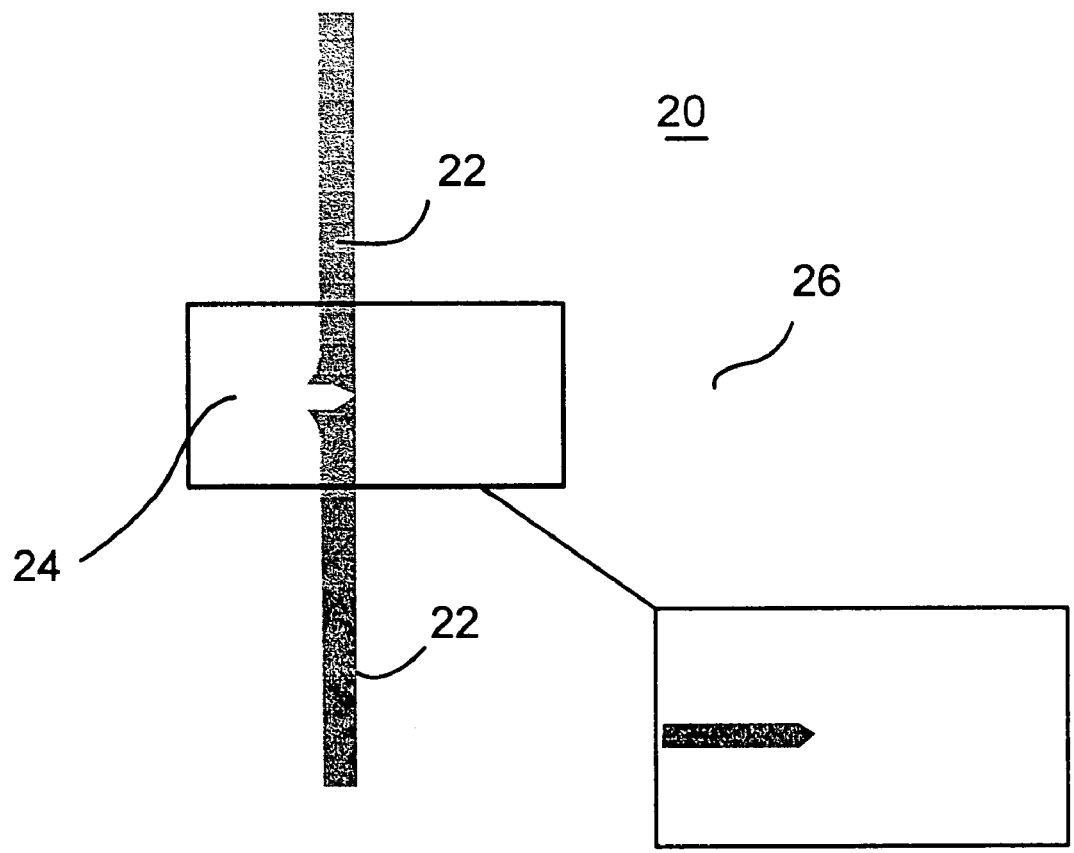

Turning now to FIG. 2, a cross flow droplet generator generally designated 20 is illustrated schematically. Nano- and micro-droplets can be formed in generator 20 using immiscible fluids, such as oil, in cross channels 22 as focusing fluid and water in central channel 24 as a carrier fluid. The carrier fluid can carry various materials such as drugs, proteins, etc. for encapsulation. The combination of flow focusing from cross channels 22 and viscous shear forces results in the formation of droplets from the continuous flows of the two phases.

Of particular interest are non-polar solvents which can dissolve lipids for the formation of liposomes in droplet generator 20. Specific non-polar solvents include ether, cyclohexane, butanol, ethyl acetate, benzyl alcohol, and the like. Ethyl acetate is of particular interest for two reasons, first it is relatively nontoxic and second it is formed from ether and acetic acid and may be broken down into its constituents at relatively low concentrations. Overall, ethyl acetate was found to be about 8% miscible in water, which means that it can eventually be exchanged into a buffer solution. In addition, unlike other immiscible oil and water solutions, it has a high vapor pressure, and may be readily separated from water by evaporation. Based on the solubility of ethyl acetate and water, this system is sufficiently immiscible to form droplets in the droplet generators while being sufficiently miscible to mix with water.

In a specific example, lipids are carried in a partially miscible solvent (e.g., ethyl acetate) and used as the focusing fluid in droplet generator 20, injected through cross channels 22. The carrier fluid (water) carries molecular beacons 12 and is injected through main channel 24. The viscous shear forces between the focusing fluid and the carrier fluid generate droplets of the carrier fluid, coated with a mono-layer of lipids (liposomes). The liposomes with a single lipid layer are carried in the focusing fluid in an outlet 26.

After liposome formation, the liposomes are flowed from outlet 26 and the focusing fluid is removed by diluting the focusing fluid in water, since the focusing fluid is partially miscible. As an example, the focusing fluid with liposomes is directed into a large volume of water (50 to 100 times larger than the volume of the focusing fluid). The focusing fluid is then dissolved into the much greater volume of water significantly reducing the concentration of focusing fluid. By repeating the wash process several times, the focusing fluid concentration is reduced to negligible levels. This is important for particles that cannot be dried for some structural or chemical reason.

In some applications it may be desirable to form more stable bi-layer liposomes. Bi-layer liposomes can be formed in accordance with a procedure described in the above identified copending application including introducing the single lipid layer liposomes into a container of excess solution with excess lipids. As there are excess lipids in the container, in order for the vesicles to remain in the aqueous buffer it is energetically favorable for them to add a second lipid layer to the single lipid layer, thus protecting the hydrophobic tail groups and presenting hydrophilic head groups to the aqueous environment both inside and outside the now fully completed liposomes. Several other methods are described in the above identified copending application for producing bi-layer liposomes if desired.

A major advantage of the droplet platform in forming liposomes (nanoparticles) is the ability to encapsulate materials such as proteins without damage. Many techniques currently being applied or investigated for drug encapsulation use high pressure or flow rates, or generate high shear forces, which can damage the structure of proteins or peptides. Since the droplet size is determined by the relative flow rates of solvent in cross channels 22 and water in main channel 24, adjusting these relative flow rates essentially varies the droplet-forming shear forces. Thus, varying the droplet size can ensure that the fragile proteins remain undamaged over a wide range of shear forces.

In one method, an assay is conducted by incubating the engineered liposomes directly with the target sample solution itself. The simplicity of this procedure makes it easier to interface the assay to standard collection equipment. Alternatively, in the event that assay sensitivity and/or response time need to be improved, the engineered liposomes are introduced into a microfluidic stream of sample solution to increase the encounter rate between the viral targets and the liposomes. Further, improvements are possible by producing droplets from a continuous flow of target fluids, and fusing them with liposome-containing droplets to initiate the assay process. Mixing is nearly instantaneous when picoliter droplets are merged in this microfluidic configuration so complex mixer structures are not needed. Also, since the aqueous droplets are individually isolated by an immiscible solvent, the risk of cross-contamination of samples is greatly reduced.

When exposed to target pathogen 16, surface receptors 18 of liposome 10 specifically bind the virus and allow the virus to fuse with lipid bilayer 14, inserting its genetic material inside liposome 10. Once inside liposome 10, the genetic material activates molecular beacons 12 to signal a viral presence. Confined to aqueous droplets dispersed in an immiscible solvent, the target sample is presented in close proximity to the liposomes, which accelerates reaction kinetics and provides response times on the order of a few hundred seconds.

As an example, one possible target of this viral based assay is the influenza virus. It is known that influenza viruses comprise a diverse mix of antigenic subtypes. Each subtype includes a specific hemagglutinin (HA) and a specific neuraminidase (NA) subtype, e.g., H5N1 or H3N2. The host range of influenza viruses is associated with differences in the specificity of HA for attachment to highly conserved sialic acid-containing receptors on susceptible cells. HAs of human viruses have a preference for sialic acid alpha 2,6-galactose beta 1,4-N-acetyl glucosamine (SA-2,6 Gal). Thus, even if the influenza virus were modified maliciously, the receptor would have to remain the same for host cell infectivity and would still be detectable with receptor decorated liposomes (e.g. liposome 10) because genetic sequences important for the viral life cycle are conserved.

For influenza, SA-2,6 Gal decorated liposomes will capture virus particles, if present, and initiate membrane fusion, which introduces RNA genetic material into the liposomes. Under appropriate conditions (pH~5.5), the RNA becomes available for hybridization. Molecular beacon probes, in conjunction with metal-enhanced fluorescence or quantum dot emitters amplify signal intensity by 10 to 1000 fold enabling low copy number detection with relatively simple optics. Other signal transduction techniques that can be employed in later generation assays include ion channels and GPCR $2^{nd}$ messenger mechanisms to broaden the utility of this approach to toxins and other chemical threats. This protocol is especially useful for detecting emerging and unknown pathogens because genes coding for receptor binding proteins and polymerases are highly conserved. Thus a broad screen for infectious agents can be developed using all known surface receptors and a generic molecular beacon for polymerases of viral origin.

Other benefits of the proposed assay include simplicity, robustness, and the ability to be highly sensitive to a wide variety of viral agents that affect human health. A significant additional advantage of this assay is that liposome "hits" can be flow sorted and collected for additional verification and identification, by PCR or by transfection into live cells. The latter is possible because the entire pathogen genome is captured rather than a specific gene sequence, which enables extensive molecular studies and the possibility of reverse engineering a vaccine. Finally, as the assay system itself is simple and has a minimum number of active components, excellent reliability can be expected in harsh environments.

In a preferred embodiment of the viral detection apparatus and methods, molecular beacon structures with quantum dot emitters and either organic or inorganic quenchers are used to detect liposome "hits". Quantum dots, or inorganic nanoparticles, are preferred emitters as they are brighter, have greater photostability, and have narrow symmetrical emission peaks compared to organic dyes. In multiplex assays, quantum dots can be excited by a common source and easily resolved in the visible/NIR (near infrared) spectrum. Furthermore, in FACS analysis there will be less cross-talk in the detection channels, which minimizes the need for compensation algorthims.

Figure 4:
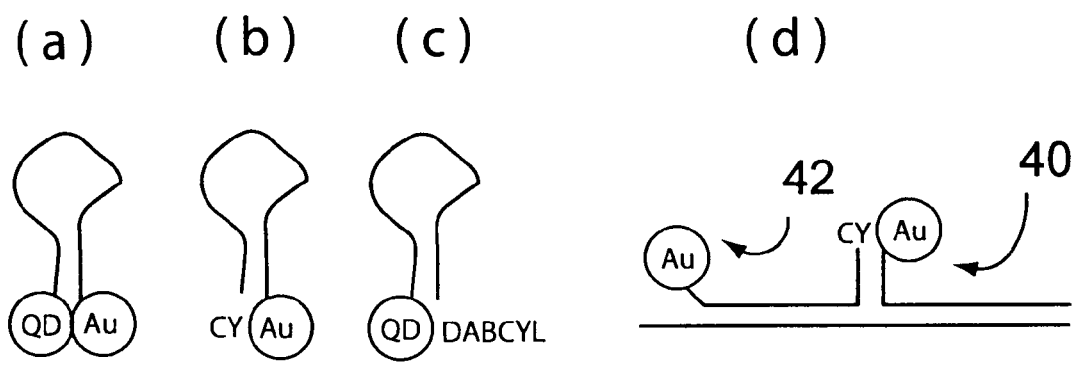

Molecular beacons consist of a stem/loop DNA structure that positions the emitter and quencher proximal to each other in the absence of a target. Examples of these molecular beacons are illustrated in FIGS. 4 (a), (b), and (c). FIG. 4 (a) illustrates a quantum dot emitter and gold particle quencher; FIG. 4 (b) illustrates a cyanine dye emitter and gold particle quencher; and FIG. 4 (c) illustrates a quantum dot emitter and DABCYL quencher. Non-radiative decay prevents photon emission upon illumination. In the presence of target analyte, the stem structure is opened by hybridization, thus separating the chromophore (emitter) from the quencher and fluorescence is observed. With organic chromophores, such as a fluorescein emitter and DABCYL quencher, the quenching efficiency is approximately 98%, providing an ON/OFF ratio of approximately 50. Quenching of dyes emitting at longer wavelength is less efficient, e.g., ~96% for Cy5 cyanine dye, because of decreased spectral overlap with the quencher. Gold or silver nanoparticles are much more efficient as quenchers over a larger spectrum and have shown as much as 100 fold increase in sensitivity by reducing the background noise.

Figure 3:
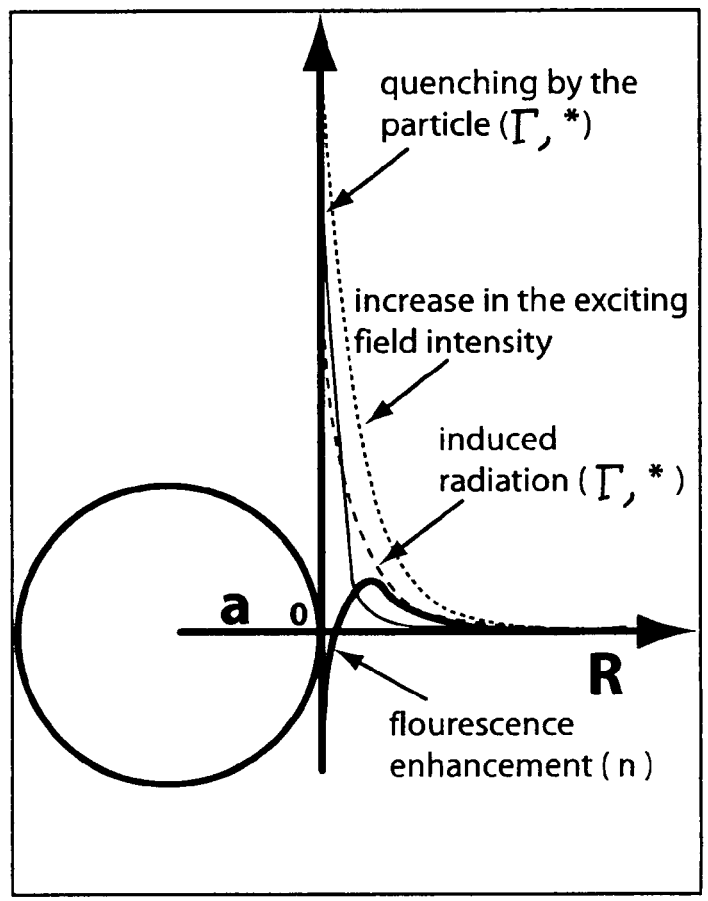

It has also been demonstrated that metal nanoparticles can enhance fluorescence by 10 to 300 fold. This apparent discrepancy in the effect of metal nanoparticles on fluorescence is related to the size of the particles used and the separation between the surface and the chromophore, as shown graphically in FIG. 3. At close range, non-radiative processes quench the fluorescence, but fluorescence enhancement is observed as the distance increases, and beyond that no enhancement is observed. The results are consistent with Forster energy transfer principles. For small particles, <30 nm, the scattering efficiency is low so surface plasmon polaritons are absorbed. At sizes >40 nm, scattering dominates the extinction coefficient so fluorescent enhancement is observed. It has also been reported that fluorescence photostability for cyanine dyes is increased by metal nanoparticles due to shorter excited state lifetime. This would also increase the maximum photon emission rates because it is proportional to inverse lifetime.

Ultimately, it is anticipated that a quantum dot signal from a single virus particle can be detected. This goal can be achieved by ensuring very low background fluorescence and significant enhancement of the fluorescent signal in the presence of a target. A sandwich hybridization configuration of a molecular beacon illustrated in FIG. 4 (d) gives the best chance for success because of the highly efficient quenching by small gold nanoparticles can be achieved for very low noise. In the presence of a target, hybridization of the molecular beacon (designated 40) and an enhancer probe that has a larger gold nanoparticle (designated 42), occurs and the fluorescent intensity increases. While a cyanine dye emitter is illustrated, it is believed that using a quantum dot emitter can achieve single molecule detection sensitivity.

Commercially marketed quantum dots from Invitrogen or Evident Technologies are available with amine, carboxyl, or sulfhydryl functional groups for coupling nucleic acids or other biocompatible layers or spacers. Unlike most organic dyes, which have only one attachment point, quantum dot nanoparticles have many functional groups. Therefore, reaction conditions are designed so that only one DNA molecule is attached to a quantum dot or gold nanoparticles. Unreacted and multiple conjugation quantum dots are separated by chromatography, which alleviates purification concerns. The chemistry and purification procedures are well described by the manufacturer and in the literature.

Alternatively, if a hybridization assay is undesirable, it has been demonstrated that fluorescent polymers such as polythiophene can react with genetic material to form triplexes. These triplexes have an extremely large stokes shift in their fluorescent spectrum, which can be detected to identify a binding event.

A major advantage of the liposome-based viral assay is its incorporation of well-established biomolecular chemistries, and the ability to perform the assay using simple fluorescence detection systems developed by cytometry. The ability to integrate the assay into cytometry platforms that can sort liposomes for follow-on verification is also significant in increasing the accuracy of the system. For example, the B-D) Becton-Dickinson) FACSAria is a high speed benchtop sorting cytometers that has 3 excitation sources and can detect 13 fluorescent colors in addition to forward and side scatter at 70,000 events/second. The FACSAria was designed to sort and maintain viable cells so it should be compatible with the present liposome process. The FACSAria can detect less than 125 molecules of equivalent soluble fluorescein (MESF). The Dako MoFlo cytometers can detect <90 MESF FITC and <40 MESF phycoerytherin. By comparison, quantum dots have a larger absorption cross-section and are about 10-20 times brighter than organic dyes. Theoretically, then, 2-4 quantum dots are detectable in the PE channel. Detection sensitivity is increased by time-gated detection to reduce autofluorescence background (2 ns lifetime) without affecting quantum dot signal (>10 ns lifetime). However, this noise reduction technique is less effective with organic chromophores that have lifetimes <4 ns.

It is estimated that at a typical cytometers flow velocity of 3 m/s, the time for a liposome to move through a 20 μm laser beam is 6.7 μs. During this transit time, a single quantum dot can emit an estimated maximum of 150-250 fluorescence photons at 50-75% quantum yields. In comparison, an estimated 7 fluorescence photons are emitted per fluorescein molecule at 90% quantum yield. Since approximately 100 MESF FITC are detected, this is equivalent to 700 photons. This suggests then that in order to detect a single quantum dot by high speed sorting FACS, a 3-5 fold enhancement of fluorescence intensity in needed. The most straightforward way to achieve that enhancement is to use multiple beacons for multiple sequences on the viral RNA within the interior of the liposome.

In nature, the influenza virus enters a target cell by binding to sialic acid residues on the cell surface, subsequently internalized by endocytosis, and finally delivered to endosomes. Virus access to the cytosol occurs following fusion of the viral envelope and the endosomal membrane that is triggered by the envelope glycoprotein, hemagglutinin, conformational changes in acidic (pH 5-6) environment of the endosomes. The proteolytic cleavage of HA produces a fusogenic protein with a hydrophobic peptide that can insert into the target membrane and induce fusion. HA-mediated fusion process is necessary for viral infectivity but not for membrane fusion. It has been reported that sialic acid gangliosides, such as GD1a or GD1b, are sufficient for virus attachment and membrane fusion. In the disclosed process, membrane fusion is all that is necessary to allow virus access to the liposome interior. The pH of the interior can be made slightly acidic to dissociate the ribonucleoprotein (RNP) and RNA complex.

Fusion occurs within 5 minutes and can be influenced by the binding affinity of HA to the sialic acid derivatives presented on the liposome surface and the membrane lipid composition. Liposome membrane composition can also be adjusted using cholesterol or nonlamellar phospholipids, such as phosphatidylethanolamine, that can induce membrane stress that is relieved by fusion events. Physicochemical parameters, such as pH and divalent cations, can also affect the fusion rate.

Cell surface receptors are glycoproteins that are embedded or otherwise attached to the cell's plasma membrane and have a binding site for specific ligands exposed to the extracellular environment. Cell surface receptors are typically integral membrane proteins and have 3 basic domains: extracellular domain (ligand-binding domain); transmembrane domain; and cytoplasmic or intracellular domain. Cell surface receptors may be purchased already purified or can be readily synthesized. To obtain membrane proteins, animals are immunized with whole cells, cell membranes that express or are engineered to over express the receptor of interest. Also, engineered peptides are used. Spleens from immunized animals are then fused with myeloma cells. The resulting hybridomas are screened for those secreting the desired antibody by cell-based ELISA, flow cytometry, or an applicable functional assay. At this point the high expressors can be expanded, protein extracted, and purified. Purification can proceed by affinity chromatography, by reverse phase high performance liquid chromatography, by ion exchange column, by pH gradient gel, by size exclusion chromatography, or by SDS-PAGE. The purified protein can be confirmed and detected by silver stain, Western blot, ELISA, or ligand binding assay.

In the case of influenza, the receptors can be much simpler, as sialic acid containing glycolipids can act as the receptors rather than an integral membrane protein. These lipids can be purchased through Avanti Polar or Sigma and used directly. Thus, there is not a need to implement the sometimes difficult and lengthy process of protein isolation, purification, and characterization in this effort. Other classes of viral targeted alternate receptors may be desired, and in those cases it is expected that commercial providers may be utilized to synthesize the receptors on either a standardized or custom basis.

The influenza surface receptor can be incorporated into the lipid membrane forming the liposomes via attachment to phospholipids or to membrane proteins. Thus, the proper insertion and orientation of membrane proteins is not a limiting factor for assay development. There are several methods to functionalize liposome surfaces with sialic acid: 1) SA residues can be conjugated to preformed liposomes with functional groups in batch mode; 2) SA-glycolipid conjugates can be exchanged into preformed liposomes in batch mode; or 3) SA-glycolipids can be incorporated into liposomes in the droplet generator in one pot real time mode. The latter method is preferred because it requires less purification steps. For these small carbohydrate receptors, random insertion into the inner or outer leaflet (first or second lipid layers of the liposome) will not materially affect virus binding and fusion.

For surface proteins that do not span the membrane bilayer, preferential incorporation of the receptor into the outer membrane leaf can be accomplished by methods 1 & 2 described above. For transmembrane proteins, insertion and orientation is evaluated by investigating signal transduction events across the lipid bilayer, such as GPCR signaling for chemical or drug interactions. For proper insertion and orientation, the simplest and most effective method seems to be optimizing the lipid composition and protein-lipid ratios to have the proteins self assemble into the correct configuration.

It will be understood that the present invention also anticipates the collection of the genetic material of pathogens and other genetic material for further experimentation and detection in, for example, a laboratory or the like. A method of collecting pathogens includes forming liposomes as described above but not including the beacons or other detecting means within the lipid shell, e.g. shell 14. Surface receptors 18 are attached to or in the surface of the shell and pathogens are attached as described above. However, the pathogens introduce or "inject" their genetic material, generally RNA but sometimes DNA, into the interior of liposome 10 by fusion with the lipid membrane, as described above, which genetic material is basically stored or collected by the process. The genetic material collected within the liposomes can then be taken to a laboratory or the like for testing, experimentation, or whatever desired use. Among the various experiments and tests that might be performed on the retained genetic material are PCR or microarray analysis using fluorescence or chemiluminescence, or hybridization techniques that can be sensitively detected using fluorescence, surface plasmon resonance, fluorescent correlation spectroscopy, fluorescence anisotropy, circular dichroism, etc.

The collected genetic material can also be merely sequestered for later destruction. In that case the fusion methodology is utilized as decontamination means for removing pathogens from the sample stream, or even from the body. Thus, a means of collecting genetic material is encapsulated within a lipid membrane and receptors are assembled in association with the membrane. The genetic material collecting means can be any material that will accept the genetic material from the pathogen or the like. By encapsulating reagents that are destructive to the genetic material, for example DNAse or RNAse, the collected genetic material may be immediately cleaved into smaller sequences and rendered harmless, as opposed to sequestering it for bulk destruction at a later time.

Thus, a new and improved method of generating viral detection liposomes using nanodroplet technology has been disclosed. Also disclosed is a novel liposome for viral detection including molecular beacons encapsulated within the liposome and receptors in or on the surrounding membrane generated in droplet generators. The nanodroplet technology represents the only technology capable of: (1) encapsulating the molecular beacons and retaining their full function; (2) producing liposomes that are monodispersed and designed to have a size optimized for use in commercial sorting flow cytometers; (3) producing fully functionalized shells with receptors for a wide variety of viral targets; and (4) achieving liposome compositions optimized to have sufficient stability for bio-defense applications and rapid diagnostics.

Various changes and modifications to the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. A virus-detecting liposome comprising:
    a plurality of molecular beacons comprising fluorescing components and strands of DNA or RNA capable of hybridizing to the genetic material of the virus:
    a lipid membrane encapsulating the plurality of molecular beacons; and
    receptors associated with the lipid membrane comprising specific binding sites for the virus that allow the virus to fuse with lipid membrane and insert its genetic material inside the liposome;
    wherein the fluorescing components comprise a fluorescent emitter and a fluorescent quencher that are proximal to each other in absence of the genetic material of the virus, and
    wherein the emitter fluorescence increases when the molecular beacon hybridizes to the genetic material of the virus.

2. A virus-detecting liposome of claim 1, wherein the fluorescing components comprise a fluorescent donor and fluorescent acceptor probe that are proximal to each other in the presence of the genetic material of the virus, and wherein the acceptor fluorescence increases by fluorescent resonant energy transfer when the donor fluorophore is excited.

3. A virus-detecting liposome as claimed in claim 2 wherein the fluorescing components comprise quantum dot emitters or organic dye emitters.

4. A virus-detecting liposome as claimed in claim 3;
    wherein the fluorescing components further comprise organic quenchers or inorganic quenchers.

5. A virus-detecting liposome as claimed in claim 1;
    wherein the molecular beacons comprise a stem/loop structure that positions an emitter and quencher proximal to each other in the absence of the genetic material of the virus.

6. A virus-detecting liposome as claimed in claim 5;
    wherein each liposome includes at least one molecular beacon having a quantum dot emitter and a gold nanoparticle quencher.

7. A virus-detecting liposome as claimed in claim 1 further comprising an enhancer probe;
    wherein the molecular beacon and enhancer probe are capable of forming a sandwich hybridization configuration with the virus genetic material.

8. A virus-detecting liposome as claimed in claim 1;
    wherein the receptors comprise sialic acid.

9. A virus-detecting liposome as claimed in claim 1 wherein the receptors are cell surface receptors embedded in and/or attached to the membrane.

10. A virus-detecting liposome as claimed in claim 9 wherein the cell surface receptors comprise glycoproteins.

* * * * *